US00PP09781P

United States Patent [19]

Proteau et al.

[11] Patent Number: Plant 9,781

[45] Date of Patent: Jan. 14, 1997

[54] POLEMONIUM PLANT NAMED BRISE D'ANJOU

[76] Inventors: Maurice Proteau; Rene Proteau, both of Les Quatre Rues, St. Saturnin-sur-Loire, 49320 Brissac-Quince, France

[21] Appl. No.: 495,974

[22] Filed: Jun. 28, 1995

[51] Int. Cl.[6] ..... A01H 5/00

[52] U.S. Cl. ..... Plt./68.1

[58] Field of Search ..... Plt./54.1, 68.1

*Primary Examiner*—James R. Feyrer

*Attorney, Agent, or Firm*—Foley & Lardner

[57] ABSTRACT

A new and distinct cultivar of Polemonium plant named Brise d'Anjou, characterized by its distinct yellow-edged variegated foliage, with violet blue flowers beginning in May and continuing to flower into August, and excellent vigor.

3 Drawing Sheets

The present invention relates to a new and distinct cultivar of hardy perennial herbaceous plant of the genus Polemonium, a member of the Polemoniaceae family, and the species *Polemonium caeruleum*, known by the cultivar name Brise d'Anjou. The species is commonly known and referred to by the commercial designation "Jacob's Ladder."

The new cultivar was discovered as a naturally occurring mutation from the parent *Polemonium caeruleum* cultivar in a cultivared area, namely, a nursery, at Brissac-Quince, France by the inventors Maurice Proteau and Rene Proteau. The new cultivar Brise d'Anjou is quite distinct from typical plants of *Polemonium caeruleum* and was discovered primarily due to its unique yellow-edged foliage which was noted as holding its variegation right through to winter.

The new cultivar was first asexually reproduced by division by, or under the supervisor of, the inventors Maurice Proteau and Rene Proteau in a controlled environment in Brissac-Quince, France. Such propagation and subsequent asexual propagation and trialing of the new cultivar have clearly demonstrated that the combination of characteristics as herein disclosed for the new cultivar are firmly fixed and are retained through successive generations of asexual reproduction.

The new cultivar possesses many of the same characteristics as other cultivars of the species, including flower form and type, flowering habit, clump-forming habit, and excellent vigor. In mild areas, Brise d'Anjou and other plants of the species will remain evergreen. Typical plants of the species form clumps which flower for many weeks, often starting as early as May and continuing until August. Plants of the species, including the new cultivar, thrive best in partial shade or in a sheltered spot, but will tolerate full sun. Well-drained soil that does not dry out provides the best growing conditions.

The new cultivar Brise d'Anjou is particularly characterized by its variegated foliage which, to the best knowledge of the inventors, is unique. The main foliage color is yellow green but there is a yellow edge of substantial dimension that varies in width depending upon the age of the leaves. The new cultivar is further characterized by its violet blue flowers, excellent vigor, and striking effect of the variegated foliage against the erect stems topped with violet blue flowers displaying rich yellow stamens. The new cultivar has a low growing habit and is ideal for use in borders or containers.

In addition to the described comparison with typical plants of the species, including the parent cultivar, Brise d'Anjou can be compared with the *Polemonium caeruleum* cultivar Dawn Flight. The habit of Brise d'Anjou is similar to Dawn Flight but the new cultivar is distinguished from Dawn Flight by its foliage color and flower color.

BRIEF DESCRIPTION OF THE PHOTOGRAPHIC DRAWINGS

The color photograph on sheet 1 is a close-up view of the plant of Brise d'Anjou, emphasizing the pinnate finely divided foliage with its unique yellow-edged leaves.

The photograph on sheet 2 is a view of the plant growing in a border setting.

The photograph on sheet 3 is a plant of Brise d'Anjou in flower, with the photograph accurately depicting the rich violet blue flower color. It should be noted that the foliage shown in this photo has a substantial yellow hue and does not accurately depict the true lamina and margin colors of the foliage.

DETAILED PLANT DESCRIPTION

The following is a detailed description of Brise d'Anjou based on plants grown in Weinheim, Germany and Diss, Norfolk, England. All color determinations and comparisons are based on The Royal Horticultural Society Colour Chart.

Classification:

*Origin.*—Naturally occurring mutation.

*Parentage.*—Mutation from unnamed *Polemonium caeruleum* cultivar.

Plant:

*Habit.*—Clump forming.

*Size.*—Mature plants are 60 cm in height with a spread of about 50 cm.

*Root system.*—Fibrous.

*Plant vigor.*—A perennial that shows vigorous and healthy growth throughout Great Britain.

*Blooming habit.*—Small showy violet blue flowers borne on erect racemose stems, arising from the base of the plant.

*Blooming period.*—From May continuing into September.

*Method of asexual propagation.*—Preferably by division, although asexual reproduction by micropropagation and basal cuttings is also possible.

*Hardiness.*—Winter hardy throughout the British Isles. Plants have survived temperatures of −8° centigrade and could probably survive at still lower temperatures. The plant has not been fully tested for maximum summer temperature tolerance above 32° C. (90° F.).

Foliage:

*Arrangement.*—Petiole arising from a short creeping rhizome, erect, simple, with opposite pinnate leaves and terminal leaf.

*Type.*—Herbaceous.

*Texture.*—Both upper and lower surfaces are smooth and dull.

*Shape.*—Generally oval to obovate, with rounded base and obtuse to acute tip; margin entire.

*Length.*—2.5 cm to 3.0 cm.

*Width.*—1 cm.

*Petiole length.*—10–20 cm.

*Margins.*—Entire.

*Apex.*—Acute.

*Base.*—Cuneate.

Flowers:

*Form.*—Single.

*Borne.*—In compact trusses.

*Petal count.*—Five of equal size.

*Petal shape.*—Saucer shaped, many display a drooping habit.

*Flower type.*—Corymbose.

*Flower size.*—2 cm in diameter.

*Carpels.*—3-celled.

*Stamens.*—Exserted, yellow 13A in color.

Color characteristics:

*Foliage.*—Mature leaves. Upper surface (outside edge): approximately 12D. Upper surface (middle): 138A. Under surface (outside edge): 150C. Under surface (middle): 138B. Variation in variegation: Early in the growing season young leaves display dominant yellow margins relative to the green midvein area. As the growing season progresses, the green color expands from the midvein toward the edges, with green dominating in mature leaves. However, even in mature leaves, the yellow edges remain. For a leaf width of 1 cm, the green variegation color ranges from 1 mm to 8 mm in width depending upon leaf maturity.

*Flowers.*—Mature flowers. Petals: 92A. Stamens: 13A.

It is claimed:

1. A new and distinct variet of Polemonium plant named Brise d'Anjou, substantially as illustrated and described.

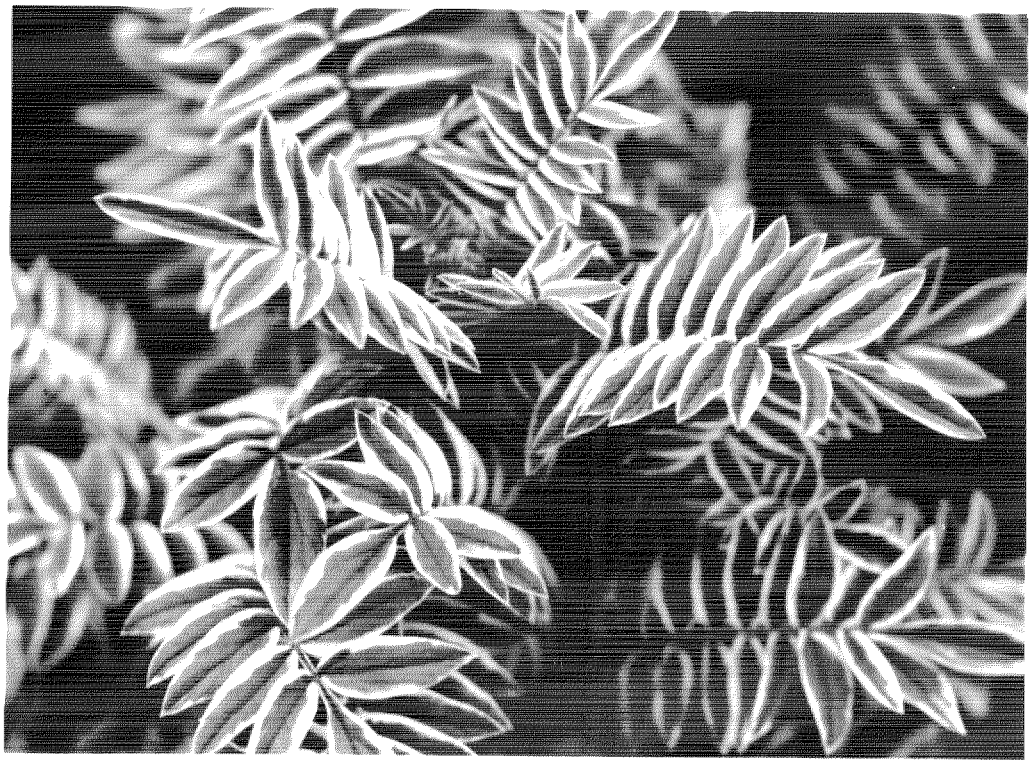

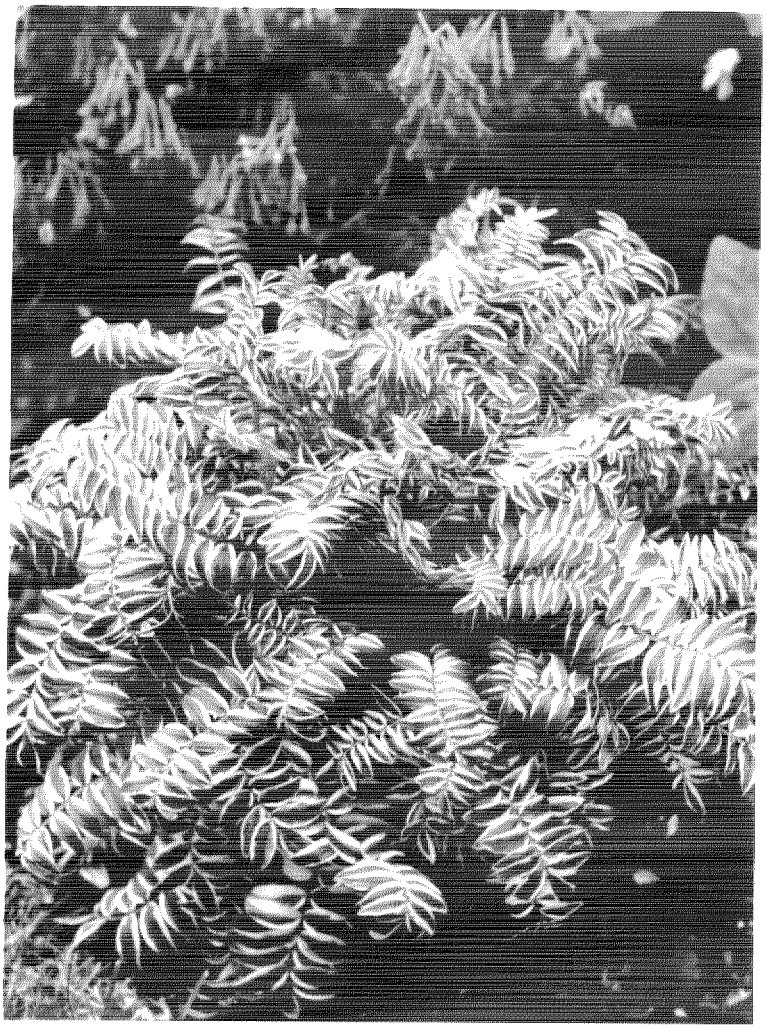

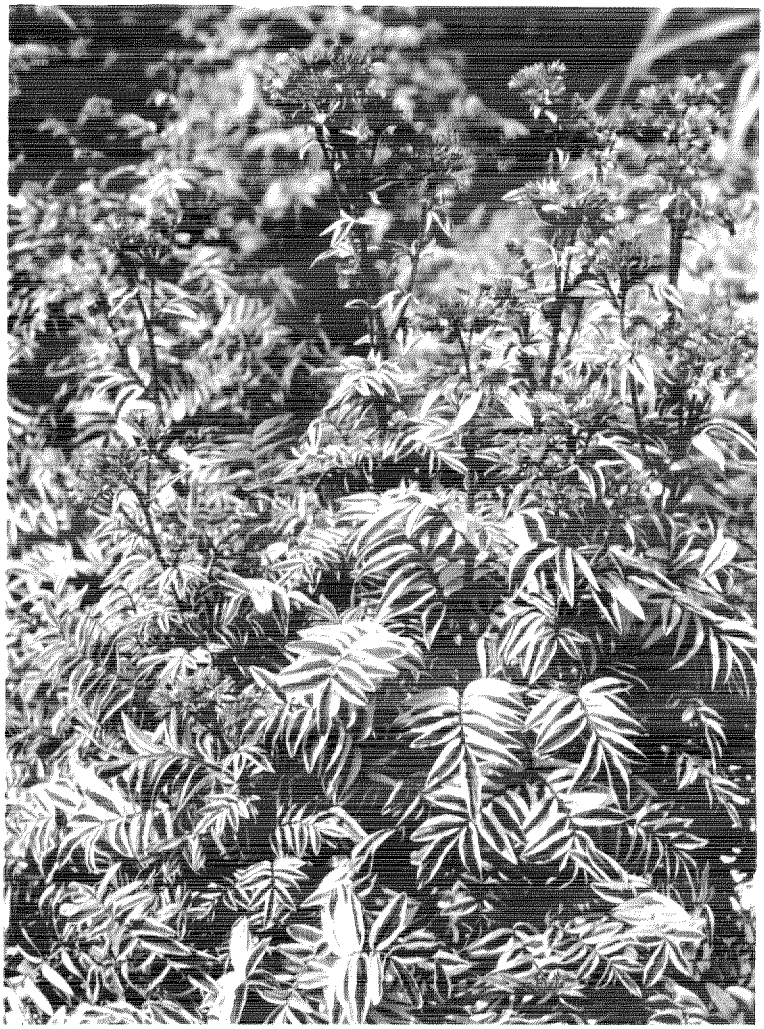

* * * * *